US00PP27438P2

(12) United States Plant Patent
Gerdts et al.

(10) Patent No.: US PP27,438 P2
(45) Date of Patent: Dec. 6, 2016

(54) NECTARINE TREE, 'BURNECTTHIRTYONE'

(50) Latin Name: ***Prunus persica* (subspecies nucipersica)**
Varietal Denomination: Burnectthirtyone

(71) Applicants: Timothy J. Gerdts, Kingsburg, CA (US); John K. Slaughter, Fresno, CA (US)

(72) Inventors: Timothy J. Gerdts, Kingsburg, CA (US); John K. Slaughter, Fresno, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 14/756,549

(22) Filed: Sep. 16, 2015

(51) Int. Cl.
*A01H 5/08* (2006.01)

(52) U.S. Cl.
USPC ..... Plt./188

(58) Field of Classification Search
USPC ..... Plt./188
CPC ..... A01H 5/0856
See application file for complete search history.

*Primary Examiner* — Kent L Bell
(74) *Attorney, Agent, or Firm* — Randall Danskin PS

(57) ABSTRACT

A new and distinct variety of nectarine tree (*Prunus persica* sub species *nuciperisica*), and which is denominated varietally as 'Burnectthirtyone', and which further produces an attractively colored firm-fleshed, low-acid, white clingstone nectarine, which is mature for harvesting and shipment approximately July 21 to July 28 under ecological conditions prevailing in the San Joaquin Valley of central California.

1 Drawing Sheet

Botanical designation: The present invention relates to a new, novel and distinct variety of nectarine tree, *Prunus persica* (subspecies *nucipersica*).

Variety denomination: Variety denomination: 'Burnectthirtyone'.

BACKGROUND OF THE NEW VARIETY

The present variety of nectarine tree resulted from an on-going program of fruit and nut tree breeding. The purpose of this program is to improve the commercial quality of available deciduous fruit and nut varieties, and rootstocks, by creating and releasing promising selections of *Prunus, Malus, Punica* and *Regia* species. To this end we make both controlled and hybrid cross pollinations each year in order to produce seedling populations from which improved progenies are evaluated and selected.

The seedling 'Burnectthirtyone' was originated by us from a population of seedlings grown in our experimental orchards which are located near Fowler, Calif. The seedlings, grown on their own roots, were the result of planting seed collected in July of 2003 of the white-fleshed clingstone nectarine tree 'J17.077', which was the seed parent. Within this seedling population one seedling, which is the present variety, exhibited especially desirable characteristics, and was subsequently designated as 'M15.078'. This newly discovered tree was then marked for subsequent observation. After the 2006 fruiting season the new variety of nectarine tree was selected for advanced evaluation and repropagation.

ASEXUAL REPRODUCTION

Asexual reproduction of the new and distinct variety of nectarine tree was accomplished by budding the new nectarine tree onto 'Nemaguard' rootstock (USDA, non-patented). This was performed by us in our experimental orchard which is located near Fowler, Calif. Subsequent evaluations have shown those asexual reproductions run true to the original tree. All characteristics of the original tree, and its fruit, were established, and appear to be transmitted through succeeding asexual propagations.

SUMMARY OF THE VARIETY

'Burnectthirtyone' is a new and distinct variety of nectarine tree, which is considered of moderately large size, and which has vigorous growth. This new nectarine tree variety is also a regular and productive bearer of relatively large, firm, white fleshed, and clingstone fruit which have good flavor and eating quality. The tree of the present variety displays a medium chilling requirement of approximately 550 hours or more. Still further, the present tree also produces relatively uniformly sized fruit throughout the tree. Additionally, the fruit produced by the present tree has a very high degree of red skin coloration, a firm flesh and further appears to have good handling and shipping qualities. The 'Burnectthirtyone' Nectarine tree bears fruit which are ripe for commercial harvesting and shipment on approximately July 23 to July 28 under the ecological conditions prevailing in the San Joaquin Valley of central California. In relative comparison to the 'Fire Pearl' nectarine (U.S. Plant Pat. No. 9,358), which is the most similar commercial variety with respect to the date of ripening, and which is known to the breeders at this time, the present, new variety, exhibits fruit that is less elongated, and more rounded than the fruit provided by the nectarine tree 'Fire Pearl'. Additionally the present variety exhibits a significantly lower degree of 'corking' in the periphery of the flesh. 'Corking' typically results from heat stress and renders the fruit non-commercial. The fruit shape provided by the new variety results in higher volumes of packable fruit; and the lower levels of 'corking' which is displayed by the 'Burnectthirtyone' will allow more fruit to be commercially packed than the closest known variety. 'Burnectthirtyone' is differentiated from its' female parent 'J17.077' in that the flesh of the new variety exhibits a higher acid level than its' female parent. In relative comparison to the pollen parent of 'J17.077', and which is an unnamed and unpatented seedling, the new variety ripens approximately 10 days later than its' male parent.

BRIEF DESCRIPTION OF THE DRAWINGS

The accompanying drawing, which is provided, is a color photograph of the new variety of nectarine tree. The photograph depicts two whole mature fruit, and one mature fruit which is dissected substantially in the sagittal plane, and which is seen from the lateral perspective. This photograph also reveals the flesh and the stone characteristics thereof. The external coloration of the fruit, as shown, is sufficiently matured for harvesting and shipment. Additionally, the photograph displays a sample vegetative shoot bearing typical leaves; a typical stone with the flesh removed; and the kernel. The colors in the photograph are as nearly true as is reasonably possible in a color representation of this type. Due to chemical development, processing, and printing, the leaves and fruit depicted in these photographs may, or may not be accurate when compared to the actual specimen. For this reason, future color references should be made to the color plates (Royal Horticultural Society Fourth Edition, 2001.) and the descriptions provided, hereinafter.

NOT A COMMERCIAL WARRANTY

The following detailed description has been prepared to solely comply with the provisions of 35 U.S.C. §112, and does not constitute a commercial warranty, (either expressed or implied), that the present variety will, in the future, display the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of nectarine tree, the following has been observed during the sixth fruiting season under the ecological conditions prevailing at orchards which are located near the town of Fowler, county of Fresno, state of California. All major color code designations are by reference to The R.H.S. Color Chart (Fourth Edition, 2001), and which is provided by The Royal Horticultural Society of Great Britain. Common color names are also occasionally used.

TREE

Size:

*Generally.*—Considered medium-large as compared to other common commercial nectarine cultivars ripening in the same season of maturity. The tree of the present variety was pruned to a height of approximately 300.0 cm to about 310.0 cm at commercial maturity.

Vigor: Considered moderately vigorous. The present variety grew from about 200.0 cm to 205.0 cm, in height, during the first growing season. The new nectarine tree variety was pruned to a height of approximately 150.0 cm during the first dormant season, and primary scaffolds were then selected for the desired tree structure.

Productivity: Productive. The fruit set varies from 2.5 to several times more than the desired crop load. The fruit set is spaced by thinning (removing excess fruit) to develop the remaining fruit into the desired market-sized fruit. The number of the fruit set varies with the prevailing climatic conditions, and the current cultural practices employed throughout the development processes of fruiting wood. Since fruit set is influenced by multiple environmental, and other cultural practice variables, the amount of fruit set is not a distinctive character of the current variety.

Bearer: Regular. Fruit set has been heavy during the period of observation, and significant thinning was necessary during the past nine growing seasons.

Form: Upright, and pruned into a vase shape.

Density: Considered medium dense. It has been discovered that pruning the branches from the center of the tree to obtain a resulting vase shape allows for proper air movement in the tree, and appropriate amounts of sunlight to be received so as to enhance fruit color and the renewal of fruiting wood throughout the entire tree.

Hardiness: The present tree was grown and evaluated in USDA Hardiness Zone 9. The winter chilling requirements of the new tree are approximately 550 hours at a temperature below 7.0 degrees C. The present variety appears to be hardy under typical Central San Joaquin Valley climatic conditions.

TRUNK

Diameter: Approximately 24.5 cm in diameter when measured at a distance of about 15.24 cm above the soil level. This measurement was taken on trees which are nine years old.

Bark texture: Considered moderately rough, and having numerous folds of papery scarfskin.

Lenticels: Numerous flat, oval lenticels are present. The lenticels range in size from approximately 4.0 to about 7.0 millimeters in width; and from about 1.0 to about 2.0 millimeters in height. It should be noted that as the bark of the trees mature, the lenticels become less apparent and also less abundant.

Lenticel color: Considered an Orange-Brown, (RHS Greyed-Orange Group 166 D).

Bark coloration: Variable, but it is generally considered to be Brown, (RHS Greyed-Orange Group 177 A).

BRANCHES

Size: Considered medium-large for the variety.

Branch diameter: Considered average as compared to other nectarine tree varieties. The branches have a diameter of about 8.0 centimeters when measured on trees which are six years old.

Branch surface texture: Average, and appearing furrowed on wood which is several years old.

Crotch angles: Primary branches are considered variable between about 45 to about 54 degrees when measured from the horizontal axis. This particular characteristic is not considered distinctive of the present variety, however.

Current season shoots:

*Surface texture.*—Substantially glabrous.

Internode length: Approximately 1.9 to about 2.4 cm. This tree characteristic is highly dependent upon the plant vigor. Plant vigor, of course, is influenced by nutrition, soil quality, pruning and tree care. Consequently this characteristic is not particularly distinctive of the new variety.

Color of mature branches: Medium-brown, (RHS Greyed-Orange 174 A).

Current season shoots:

*Color.*—Yellow green, (RHS Yellow-Green Group 144 B). The color of the new shoot tips is considered a bright, yellow green (RHS Green Group 139 B).

LEAVES

Size: Considered medium-large for the species. Leaf measurements have been taken from vigorous, upright, current-season growth, which is taken at approximately mid-shoot.

Leaf length: Approximately 138.0 to about 154.0 millimeters.

Leaf width: Approximately 36.0 to about 40.0 millimeters.

Leaf base shape: Slightly oblique relative to the longitudinal axis of the leaf.

Leaf form: Lancelolate.

Leaf tip form: Acuminate.

Leaf color:

*Upper surface.*—Dark green, (approximately RHS Green Group 139 A).

Leaf texture: Glabrous.

Leaf color:

*Lower surface.*—Medium green, (RHS Green Group 141 B).

Leaf venation: Pinnately veined.

Mid-Vein:

*Color.*—Light, yellow-green, (RHS Yellow-Green Group 144 C).

Leaf margins:

*Generally.*—Slightly undulating.

*Marginal form.*—Considered crenate, occasionally doubly crenate.

*Marginal uniformity.*—Considered generally uniform.

Leaf petioles:

*Size.*—Considered medium long.

*Length.*—About 7.0 to about 10.0 mm.

*Diameter.*—About 2.0 to about 2.5 mm.

*Color.*—Pale green, (RHS Yellow-Green Group 144 A).

Leaf glands:

*Size.*—Considered generally small. About 1.0 mm in height, and about 2.0 mm in width.

*Number.*—Generally one per side, occasionally two per side may be found. Only rarely are glands absent.

*Type.*—Reniform.

*Color.*—Orange brown, (RHS Greyed-Orange Group 177 A).

Leaf stipules:

*Size.*—Medium for the variety.

*Number.*—Typically 2 per leaf bud, and up to 6 per shoot tip can be seen.

*Form.*—Lanceolate in form, and having a serrated margin.

*Color.*—Green, (RHS Green Group 141 A) when juvenile, but then graduating to a brown color, (RHS Greyed-Orange Group 177 B) with advancing senescence. The stipules are considered to be early deciduous.

FLOWERS

Flower buds:

*Generally.*—The floral buds, depending upon the stage of development, are approximately 8.0 millimeters wide; about 13.0 millimeters long; conic in form; and slightly appressed relative to the bearing shoot.

Flower buds:

*Color.*—The bud scales are reddish-brown, (approximately RHS Greyed Purple Group 183 B). The flower buds are considered hardy under typical central San Joaquin Valley climatic conditions.

Hardiness: No winter injury has been noted during the last several years of evaluation in the central San Joaquin Valley. The current variety has not been intentionally subjected to drought or heat stress, and therefore this information is not presently available.

Date of first bloom: The date of first bloom, in 2015, was observed on February 14.

Blooming time: Considered early to mid-season in relative comparison to other commercial nectarine cultivars grown in the central San Joaquin Valley. The date of full bloom was first observed on Feb. 21, 2015. The date of full bloom varies, somewhat slightly, with the prevailing climatic conditions, and cultural practices which are employed.

Duration of the bloom: Approximately 10 days. This characteristic varies slightly with the prevailing climatic conditions.

Flower type: The variety is considered to have a showy-type flower.

Flower size: The flower diameter at full bloom is approximately 41.0 to about 46.0 millimeters.

Bloom quantity: Considered abundant.

Flower bud frequency: Normally 2 flower buds appear per node. On occasion 1 bud per node may be observed. Only rarely are more than 2 flowers buds per node observed.

Petal size:

*Generally.*—Considered average for the species.

Petal length: Approximately 16.0 to about 19.0 millimeters.

Petal width: Approximately 9.0 to about 12.0 millimeters.

Petal form: Rotund to slightly ovate.

Petal count: Typically 5.

Petal texture: Glabrous.

Petal color: Somewhat variable from a light pink, (RHS Red-Purple Group 62 B), to a medium pink, (RHS Red-Purple Group N57 C).

Fragrance: Considered slight.

Petal claw:

*Form.*—The claw is considered inversely triangular, wedge-like in shape, and having rounded angles. The petal claw is considered generally small in size when compared to other varieties.

*Length.*—Approximately 8.0 to about 12.0 millimeters.

*Width.*—Approximately 6.0 to about 9.0 millimeters.

Petal margins: Generally considered variable, from nearly smooth, to moderately undulate.

Petal apex:
*Generally.*—The petal apices appear entire with a broad, shallow apical groove.
Flower pedicel:
*Length.*—Considered medium, and having an average length of approximately 4.0 to about 6.0 millimeters.
*Diameter.*—Considered average, approximately 2.0 to about 3.0 millimeters.
*Color.*—A pale green when the bud scales are removed, (RHS Greyed-Green Group 195 A).
Floral nectaries:
*Color.*—An orange-brown, (RHS Yellow-Green Group 145 C).
Calyx:
*Surface texture.*—Generally glabrous.
*Color.*—A dull red, (approximately RHS Greyed-Red Group 178 A).
Sepals:
*Surface texture.*—The surface has a short, fine, pubescent texture.
*Size.*—Average; and ovate in form.
*Color.*—A dark, reddish purple, (approximately RHS Greyed-Purple Group 187C).
Anthers:
*Generally.*—Small in size.
*Color.*—Red to reddish-purple, (approximately RHS Greyed-Purple Group 187 D) prior to dehiscence.
Pollen production: Pollen is abundant, and has a yellow color, (approximately RHS Yellow Group 11 A).
Filaments:
*Size.*—Variable in length, approximately 14.0 to about 17.0 millimeters in length.
*Color.*—Considered a pale pink, (RHS Red-Purple Group 65 C) at maturity.
Pistil:
*Numbers.*—Normally 1, very rarely 2.
*Size.*—Considered average.
*Length.*—Approximately 19.0 to about 21.0 millimeters including the ovary.
*Color.*—Considered a very pale green, (approximately RHS Yellow-Green Group 145 C).
*Surface texture.*—The variety has a long glabrous pistil.

FRUIT

Maturity when described: Firm ripe condition (shipping ripe).
*Date of first picking.*—Jul. 21, 2015.
*Date of last picking.*—Jul. 28, 2015. The date of harvest varies slightly with climatic conditions.
Size:
*Generally.*—Considered large, and uniform.
Average cheek diameter: Approximately 72.0 to about 74.0 millimeters.
Average axial diameter: Approximately 71.0 to about 74.0 millimeters.
Typical weight: Approximately 270.0 grams. This characteristic is highly dependent upon the prevailing cultural practices, and therefore is not particularly distinctive of this new variety.
Fruit form:
*Generally.*—Rounded relative to its axis. The fruit is generally uniform in symmetry.
Fruit suture: Shallow, and extending from the mid-equatorial region to the apex. No apparent callousing or stitching exists along the suture line.
Suture:
*Color.*—The background color appears to be a medium white, (approximately RHS Group 15 B), with some occasional red coloration, (approximately RHS Red Group 46 A).
Ventral surface:
*Form.*—Full.
Apex:
*Shape.*—Rounded.
Base:
*Shape.*—Slightly retuse.
Stem cavity:
*Shape.*—Rounded and relatively shallow. The average depth of the stem cavity is about 1.0 cm. The average width of the stem cavity is about 2.4 cm.
Fruit skin:
*Thickness.*—Considered medium in thickness; and tenacious to the flesh.
*Texture.*—Glabrous.
*Taste.*—A slight astringency is noted.
*Tendency to crack.*—Cracking has not been observed. Russeting has not been observed to date on the oldest fruit bearing trees.
Blush color: The blush color is variable from a medium red, (approximately RHS Red Group 44 A), to a dark red, (approximately RHS Red Group 46 A). The blush color ranges from approximately 70% to about 85% of the fruit surface depending upon the sunlight exposure, and prevailing growing conditions.
Ground color: Generally a light yellow, (approximately RHS Yellow-Orange Group 15 B).
Fruit stem: Moderate in length, approximately 6.0 to about 9.0 millimeters.
Use: The new variety 'Burnectthirtyone' is considered to be a Nectarine tree which matures early in the season, and which further produces fruit, which are considered firm, attractively colored, and are useful for both local and long distance shipping.
Keeping quality: Appears excellent. Fruit has stored well for up to 30 days after harvest at 1.0 degree Celsius.
Shipping quality: Good. The fruit of the new nectarine tree variety displayed minimal bruising of the flesh, or skin damage, after being subjected to normal harvest and packing procedures.
Resistance to insects and disease: No particular susceptibilities were noted. The present variety has not been tested to expose or detect any susceptibilities or resistances to any known plant and/or fruit diseases.

Although the new variety of nectarine tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety nectarine tree, what we claim is new and desire to secure by plant Letters Patent is:

1. A new distinct variety of nectarine tree, substantially as illustrated and described, and which is characterized principally as to novelty by producing an attractively colored, firm-fleshed, low-acid, white, clingstone nectarine which is mature for harvesting and shipment approximately July 21 to July 28 under the ecological conditions prevailing in the San Joaquin Valley of central California.

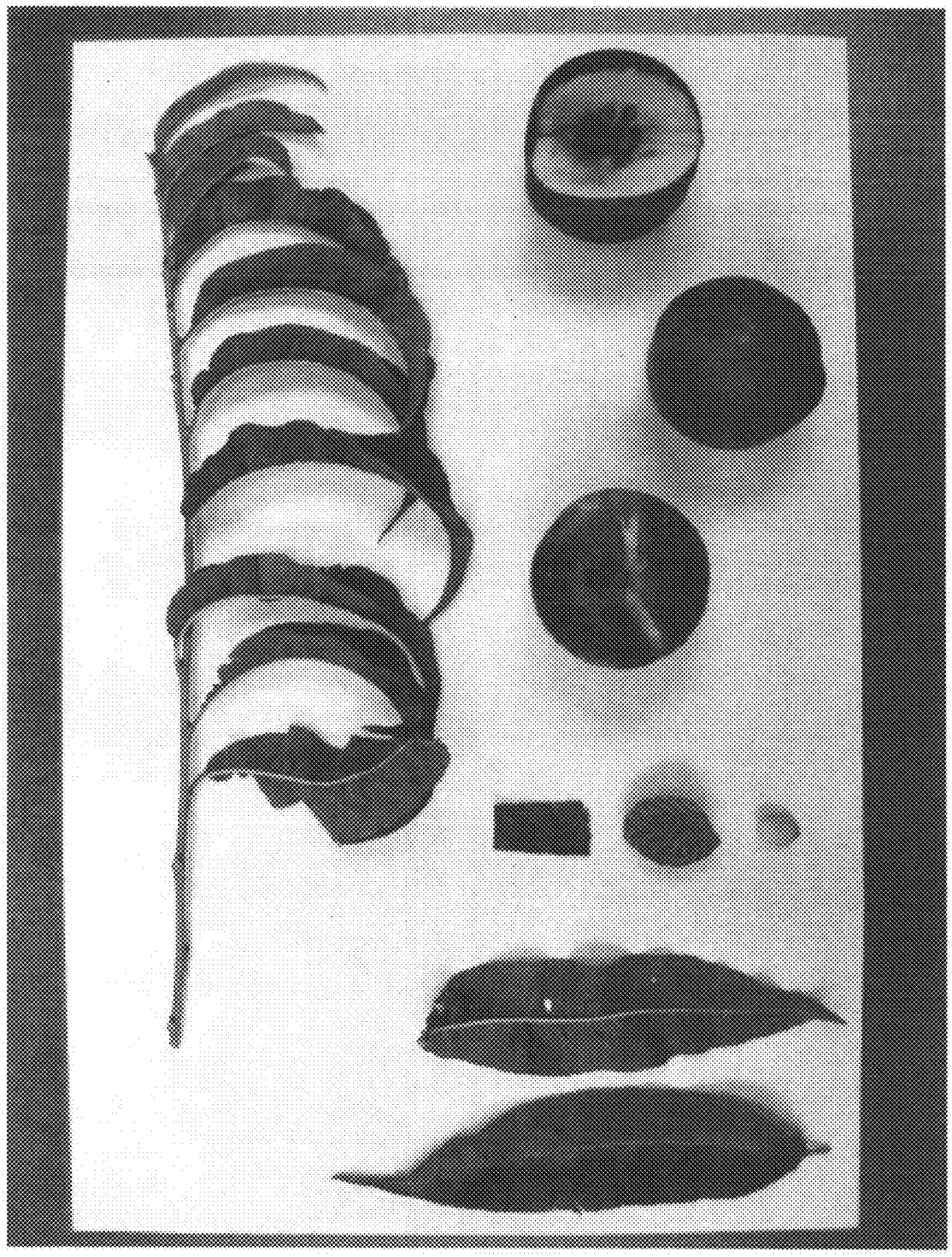

* * * * *